US009655666B2

(12) United States Patent
Markowitz et al.

(10) Patent No.: US 9,655,666 B2
(45) Date of Patent: May 23, 2017

(54) CATHETER WITH CORONARY SINUS OSTIUM ANCHOR

(75) Inventors: H. Toby Markowitz, Roseville, MN (US); Amy E. Thompson-Nauman, Coon Rapids, MN (US)

(73) Assignee: Medtronic Ablatio Frontiers LLC, Minneapolis, MN (US)

( * ) Notice: Subject to any disclaimer, the term of this patent is extended or adjusted under 35 U.S.C. 154(b) by 1544 days.

(21) Appl. No.: 12/915,327

(22) Filed: Oct. 29, 2010

(65) Prior Publication Data

US 2012/0108953 A1    May 3, 2012

(51) Int. Cl.
| | |
|---|---|
| A61B 18/14 | (2006.01) |
| A61B 18/02 | (2006.01) |
| A61B 5/042 | (2006.01) |
| A61B 18/00 | (2006.01) |
| A61M 25/04 | (2006.01) |
| A61B 90/00 | (2016.01) |

(52) U.S. Cl.
CPC ............. *A61B 18/02* (2013.01); *A61B 5/042* (2013.01); *A61B 18/1492* (2013.01); *A61B 2018/00023* (2013.01); *A61B 2018/00214* (2013.01); *A61B 2018/00273* (2013.01); *A61B 2018/00285* (2013.01); *A61B 2018/00755* (2013.01); *A61B 2018/00875* (2013.01); *A61B 2018/00898* (2013.01); *A61B 2090/0811* (2016.02); *A61M 25/04* (2013.01)

(58) Field of Classification Search
CPC .................. A61B 2018/1492; A61B 2018/0022–2018/00261; A61B 2018/00273–2018/00285; A61B 2018/00351; A61B 2018/00374; A61B 2018/00386; A61B 18/1492; A61B 2018/00267
USPC ......................................... 606/41
See application file for complete search history.

(56) References Cited

U.S. PATENT DOCUMENTS

| | | | |
|---|---|---|---|
| 4,753,637 | A | 6/1988 | Horneffer |
| 5,718,241 | A | 2/1998 | Ben-Haim et al. |
| 5,725,521 | A | 3/1998 | Mueller |
| 6,533,751 | B2 | 3/2003 | Cragg et al. |
| 6,785,571 | B2 | 8/2004 | Glossop |
| 7,144,363 | B2 | 12/2006 | Pai et al. |
| 7,309,354 | B2 | 12/2007 | Mathis et al. |

(Continued)

FOREIGN PATENT DOCUMENTS

WO    2006010908 A1    2/2006

*Primary Examiner* — Joseph Stoklosa
*Assistant Examiner* — Eunhwa Kim
(74) *Attorney, Agent, or Firm* — Christopher & Weisberg, P.A.

(57) ABSTRACT

A method of treating cardiac tissue is provided, including positioning a first chamber of a medical device adjacent an atrial wall; directing a cryogenic coolant into the first chamber; anchoring the first chamber to the atrial wall through cryoadhesion; directing a distal portion of the medical device into the coronary sinus; and positioning a cardiac lead through at least a portion of the coronary sinus with the distal portion. The method may include measuring a temperature of the first chamber; removing the first chamber from the atrial wall once a predetermined threshold temperature of the first chamber is reached; anchoring a second chamber of the medical device to a portion of the coronary sinus; and/or perfusing blood flow through at least a portion of the second chamber.

13 Claims, 5 Drawing Sheets

(56) References Cited

U.S. PATENT DOCUMENTS

| | | | |
|---|---|---|---|
| 2001/0021849 A1* | 9/2001 | Swartz et al. | 606/41 |
| 2002/0002371 A1* | 1/2002 | Acker et al. | 606/27 |
| 2002/0017306 A1 | 2/2002 | Cox et al. | |
| 2002/0045810 A1* | 4/2002 | Ben-Haim | 600/374 |
| 2002/0045893 A1* | 4/2002 | Lane | A61B 18/02 606/21 |
| 2002/0100482 A1* | 8/2002 | Sterman | A61M 25/0026 128/898 |
| 2003/0069523 A1* | 4/2003 | Williams et al. | 600/585 |
| 2003/0176830 A1* | 9/2003 | Scheule | A61M 1/3653 604/6.16 |
| 2003/0199938 A1* | 10/2003 | Smits et al. | 607/27 |
| 2004/0097806 A1* | 5/2004 | Hunter | A61B 1/00071 600/434 |
| 2004/0158237 A1 | 8/2004 | Abboud et al. | |
| 2005/0197568 A1 | 9/2005 | Vass et al. | |
| 2005/0215989 A1* | 9/2005 | Abboud et al. | 606/21 |
| 2006/0084884 A1* | 4/2006 | Beatty et al. | 600/523 |
| 2006/0089694 A1* | 4/2006 | Zhang et al. | 607/122 |
| 2006/0106420 A1 | 5/2006 | Dolan et al. | |
| 2006/0241737 A1* | 10/2006 | Tockman et al. | 607/126 |
| 2006/0258980 A1 | 11/2006 | Bridges et al. | |
| 2007/0103437 A1* | 5/2007 | Rosenberg | G09B 23/285 345/161 |
| 2008/0009747 A1* | 1/2008 | Saadat et al. | 600/471 |
| 2009/0005769 A1* | 1/2009 | Haywood | 606/21 |
| 2009/0054823 A1 | 2/2009 | Bridges et al. | |
| 2009/0088735 A1* | 4/2009 | Abboud et al. | 606/22 |
| 2009/0093801 A1* | 4/2009 | Crossman | A61B 18/1492 606/21 |
| 2009/0228100 A1 | 9/2009 | Solem et al. | |
| 2009/0253976 A1* | 10/2009 | Harlev | A61B 5/0422 600/374 |
| 2009/0262109 A1* | 10/2009 | Markowitz et al. | 345/419 |
| 2009/0287185 A1 | 11/2009 | Bridges | |

* cited by examiner

CATHETER WITH CORONARY SINUS OSTIUM ANCHOR

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to methods and systems for cardiac treatment and, more particularly, to systems and methods of use thereof facilitating the positioning of minimally-invasive devices in confined, tortuous physiological areas.

BACKGROUND OF THE INVENTION

During a number of interventional procedures related to cardiac treatment, a physician manipulates catheters and/or leads inside the heart chambers and associated vasculature. Two such cardiac procedures include the treatment of an arrhythmia (such as atrial fibrillation) and cardiac pacing. Atrial fibrillation, which refers to an arrhythmia in which the atria (upper chambers of the heart) stop contracting as they fibrillate, is the most commonly experienced heart rhythm abnormality. Both treatment procedures involve directing a catheter or other intravascular device to designated areas in or about the chambers of the heart. For example, an arrhythmia treatment procedure may include directing an ablation device through a blood vessel leading to the heart for subsequent treatment of portions of an atrial wall where the problematic tissue is located. Biventricular pacing also involves the routing and positioning of one or more intravascular devices in proximity to specific locations of the heart, such as the coronary ostium.

A common technique facilitating or easing the directing and placement of the selected medical devices within the heart involves fluoroscopic imaging. However, numerous factors render current approaches using current fluoroscopically guided techniques somewhat cumbersome and lengthy for arrhythmia treatment, such as inadequate three-dimensional reconstruction of the left atrium using some currently available technologies, the inability of the physician to visualize particular tissue sites (such as the pulmonary vein ostia), the varying size of the pulmonary veins and thus the pulmonary vein ostia, the difficulty in keeping the selected medical devices stable at the pulmonary vein ostia and other important sites in the left atrium due to the complex geometry of these areas.

Similar difficulties are present for placing cardiac leads or other diagnostic and therapeutic devices within the coronary sinus. The anatomical structures in and around the coronary sinus itself are not depicted very well by typical fluoroscopic systems since they do not present sufficient contrast to the surrounding anatomical structures. Moreover, cannulating the coronary sinus may be challenging as a result of an enlarged right atrium, rotation of the heart, or presence of a Thebesian valve (a valve close to the opening of the coronary sinus), and coronary sinus stenosis (occlusion) has also been reported in patients with prior coronary artery bypass surgery, further complicating the intended treatment procedure.

The difficulties described above may result in extended times to complete a designated procedure and potentially expose patients to undesired risks associated with such prolonged procedures. In view of such limitations and difficulties, there remains a need in the art for improved methods and apparatus for expeditiously directing and placing medical devices in and around the heart for subsequent diagnosis or treatment.

SUMMARY OF THE INVENTION

The present invention advantageously provides methods and apparatus for directing and placing medical devices in and around the heart for subsequent treatment. In particular, a medical device is provided, including an elongate body having a proximal portion and a distal portion; an electrode on the distal portion; a chamber positioned on the elongate body between approximately 1 cm to 10 cm proximally of the electrode; and a cryogenic coolant source in fluid communication with the chamber. The chamber may be defined by a balloon, and the device may also include a temperature sensor in thermal communication with the chamber; an expandable chamber disposed on the elongate body between the first chamber and the electrode; at least one of an electrical current generator, a voltage sensing apparatus, and an electrical property assessment device in electrical communication with the electrode, such as a cardiac pacing/stimulation and/or radiofrequency signal source, a voltage measuring apparatus, an impedance measurement device, or the like.

A method of operating a medical device in a patient is provided, including positioning a first chamber of a medical device adjacent a first tissue region; directing a cryogenic coolant into the first chamber; anchoring the first chamber to the first tissue region through cryoadhesion; positioning at least one of a diagnostic element and a therapeutic element of the medical device adjacent a second tissue region; and operating the at least one of a diagnostic element and therapeutic element proximate to the second tissue region. The diagnostic element or therapeutic element may include a cardiac lead or a thermal ablation element, and operating the ablation element may include ablating at least a portion of the second tissue region. Positioning the diagnostic element or therapeutic element may include moving the diagnostic element or therapeutic element with respect to the first chamber. The first tissue region may include cardiac tissue; the second tissue region may include a portion of the coronary sinus; and the method may also include anchoring a second chamber of the medical device to a portion of the coronary sinus; measuring a temperature of the first chamber; obtaining positional information of the at least one of a diagnostic element and a therapeutic element; and/or storing the positional information. Obtaining positional information may include at least one of conducting a current through the diagnostic element or therapeutic element and/or measuring a voltage with the at least one of a diagnostic element and a therapeutic element. The method may also include determining an impedance between the diagnostic or therapeutic element and a reference electrode located on or in the patient. The method may also include obtaining positional information of the first chamber and storing the positional information, where obtaining positional information includes at least one of conducting a current through at least a portion of the first chamber and/or measuring a voltage with at least a portion of the first chamber. The method may also include registering the obtained positional information to a historical positional information set and/or determining an impedance between the portion of the first chamber and a reference electrode located on or in the patient.

A method of treating a patient is also provided, including performing a first procedure, the first procedure including: positioning at least one of a diagnostic element and a therapeutic element of a first medical device adjacent a first tissue region; operating the at least one of a diagnostic element and therapeutic element proximate to the first tissue region; obtaining positional information of the at least one of a diagnostic element and a therapeutic element; generating a first map based on the positional information; and performing a second procedure, the second procedure including: positioning at least one of a diagnostic element and a therapeutic element of a second medical device adjacent a second tissue region; operating the at least one of a diagnostic element and therapeutic element proximate a tissue region; obtaining positional information of the at least one of a diagnostic element and a therapeutic element; generating a second map based on the positional information; registering the second map to the first map. The first procedure may include positioning a first chamber of the first medical device adjacent a third tissue region different from the first tissue region; and anchoring the first chamber to the third tissue region. The second procedure may include positioning a first chamber of the second medical device adjacent a fourth tissue region different from the second tissue region; and anchoring the first chamber to the fourth tissue region. Also, the first tissue region and the second tissue region may be substantially co-located or otherwise include substantially the same tissue region within the patient.

A method of treating cardiac tissue is also provided, including directing a distal portion of a medical device into a coronary sinus; positioning a first chamber of a medical device adjacent an atrial wall; directing a cryogenic coolant into the first chamber; anchoring the first chamber to the atrial wall through cryoadhesion; and positioning a cardiac lead through at least a portion of the coronary sinus with the distal portion. The method may include measuring a temperature of the first chamber; evacuating coolant from the first chamber; and/or removing the first chamber from the atrial wall once a predetermined threshold temperature of the first chamber is reached. The method may also include anchoring a second chamber of the medical device to a portion of the coronary sinus, where anchoring the second chamber includes introducing a cryogenic fluid into the second chamber to cryoadhere the second chamber to the coronary sinus; and/or perfusing blood flow through at least a portion of the second chamber.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 1a is an illustration of an embodiment of an anchoring element for a medical device constructed in accordance with the principles of the present invention;

FIG. 1b is another illustration of an embodiment of an anchoring element for a medical device constructed in accordance with the principles of the present invention;

DETAILED DESCRIPTION OF THE INVENTION

Figure 1:
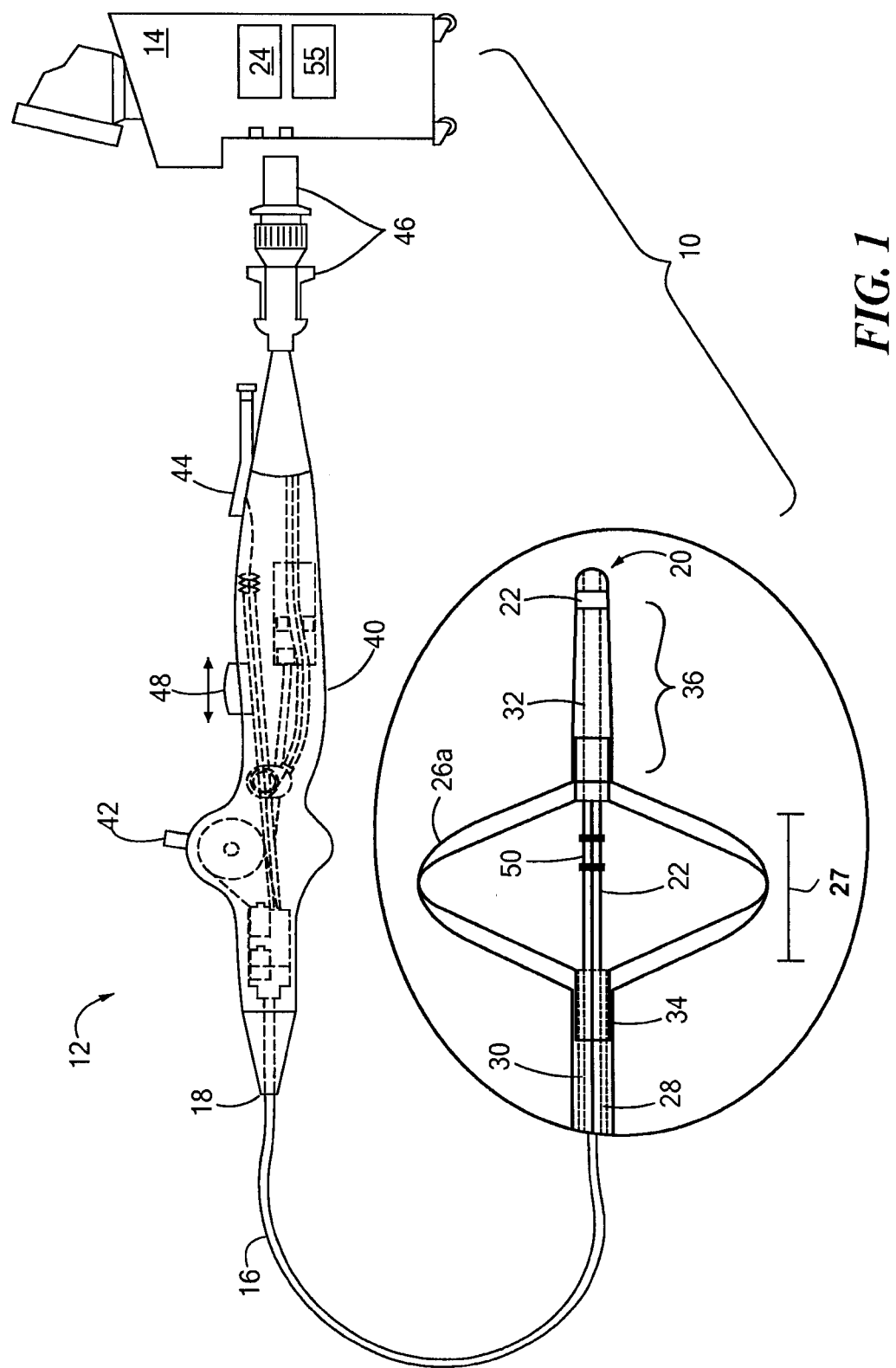
FIG. 1 is an illustration of an embodiment of a medical system constructed in accordance with the principles of the present invention.

The present invention advantageously provides methods and apparatus for expeditiously directing and placing medical devices in and around the heart for subsequent diagnosis or treatment. Referring now to the drawing figures in which like reference designations refer to like elements, an embodiment of a medical system constructed in accordance with principles of the present invention is shown in FIG. 1 and generally designated as "10." Of note, the device components have been represented where appropriate by conventional symbols in the drawings, showing only those specific details that are pertinent to understanding the embodiments of the present invention so as not to obscure the disclosure with details that will be readily apparent to those of ordinary skill in the art having the benefit of the description herein. Moreover, while certain embodiments or figures described herein may illustrate features not expressly indicated on other figures or embodiments, it is understood that the features and components of the system and devices disclosed herein are not necessarily exclusive of each other and may be included in a variety of different combinations or configurations without departing from the scope and spirit of the invention.

Referring now to FIG. 1, the system 10 generally includes a medical device 12 that may be coupled to a control unit or operating console 14. The medical device 12 may include an elongate body 16 passable through a patient's vasculature and/or proximate to a tissue region for diagnosis or treatment, such as a catheter, sheath, or intravascular introducer. The elongate body 16 may define a proximal portion 18 and a distal portion 20, and may further include one or more lumens disposed within the elongate body 16 thereby providing mechanical, electrical, and/or fluid communication between the proximal portion 18 of the elongate body 16 and the distal portion 20 of the elongate body 16, as discussed in more detail below.

The medical device 12 may further include a diagnostic or treatment element(s) 22 on the distal portion 20 of the elongate body 16 for assessing or measuring a property or characteristic of a tissue site (e.g., cardiac signal mapping, tissue composition assessments, tissue contact assessment, or the like) and/or for delivering or otherwise transmitting a therapeutic or diagnostic signal or energy to a tissue site (e.g., electrical energy delivery, tissue ablation, cardiac pacing, or the like). The treatment element(s) 22 may deliver, for example, radiofrequency energy, cryogenic therapy, or the like to a tissue area in proximity to the distal portion 20 of the medical device 12. For example, the diagnostic or treatment element 22 may include one or more electrodes or electrically conductive portions of electrodes. The electrode(s) may include variations in their number, arrangement, configuration, or shape and may be constructed from conductive materials such as silver, platinum or gold, for example. The electrode(s) may constitute an electrically conductive portion operable as a temporarily positionable or implantable cardiac lead for cardiac pacing and/or other electrophysiological functions or treatments. The electrode(s) may be coupled to or otherwise be in electrical communication with a power delivery and/or measurement source 24 in the control unit 14 operable to deliver or measure a characteristic of a particular energy (such as a radiofrequency ablation signal, a cardiac pacing signal, or other therapeutic or diagnostic signal, and/or properties thereof, for example) to the medical device 12 during a designated medical procedure.

The medical device 12 may include one or more anchoring elements 26a to facilitate the secure placement or coupling of a portion of the medical device 12 to a designated or selected tissue site, such as within one or more chambers of a heart or its associated vascular pathways. The anchoring element 26a may be located along a length of the elongate body 16 with sufficient distance from the distal portion 20 and/or the diagnostic/treatment element 22 to allow the secure placement of the anchoring element 26a while permitting the distal portion 20 and/or the diagnostic/treatment element 22 to be manipulated or otherwise positioned and re-positioned around a particular physiological region or structure (and vice versa). In particular, the anchoring element 26a may be located between approximately 1 cm and 10 cm proximally of the treatment element 22. The spacing between the anchoring element 26a and the treatment/diagnostic element 22 may allow the anchoring element 26a to engage a portion of the right atrial wall, while allowing the treatment element 22 to be maneuvered and directed into and around portions of the coronary sinus, for example.

The anchoring element 26 a may include a thermally conductive segment defining an interior chamber or fluid circulation passage allowing the introduction of a fluid, such as a cryogenic coolant therein. The anchoring element 26 a may thus have its temperature significantly reduced to enable cryoadhesive engagement between the anchoring element 26 a and an adjacent or nearby tissue structure or region. As used herein, cryoadhesion is referred to as the contact freezing and resulting bond (which is facilitated by the moisture on the tissue) formed between a cryogenically cooled structure and the adhered tissue segment. The anchoring element 26 a may include an expandable element, such as a balloon, that can be inflated or otherwise expanded to contact and engage tissue in its proximity. The expandable element may have any of a myriad of shapes, and may further include one or more material layers providing for puncture resistance, radiopacity, or the like. In addition, the anchoring element 26 a and/or a portion thereof 27 may be electrically conductive and coupled to an electrical signal generator and/or electrical measurement and/or sensing apparatus, as described in more detail below. The expandable element may circumscribe a portion of the elongate body 16 in a substantially coaxial configuration, or may alternatively traverse only a portion of the circumference of the elongate body 16 or have an otherwise eccentric configuration. The elongate body 16 may include an injection lumen 28 and an exhaust lumen 30 defining a fluid flow path therethrough in fluid communication with an interior chamber defined by the expandable element. In addition, the fluid injection and/or exhaust lumens may be slidably positionable and movable within the expandable element to direct coolant or fluid dispersion towards a desired portion of the expandable element, such as distal or proximal portion 18.

Figure 1C:
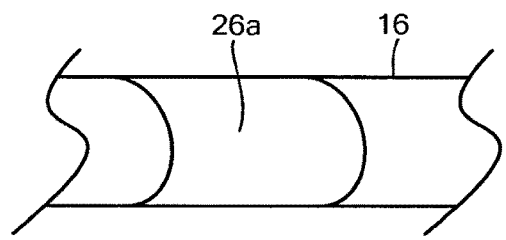
FIG. 1c is yet another illustration of an embodiment of an anchoring element for a medical device constructed in accordance with the principles of the present invention.
Figure 1C:
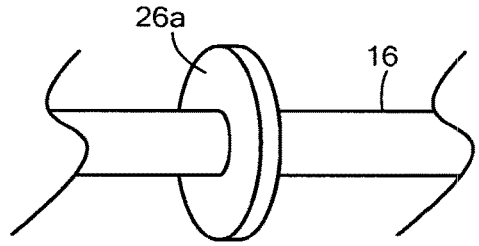
Figure 1C:
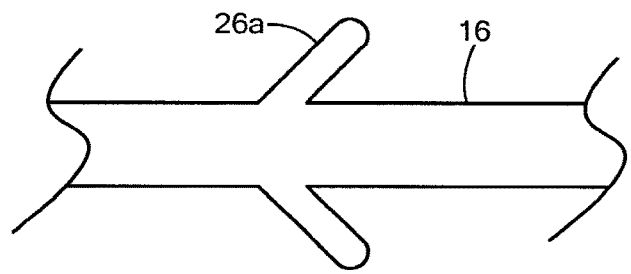

The anchoring element 26a may include a variety of configurations in addition or alternatively to the expandable element described above. For example, as shown in FIG. 1a, the anchoring element 26a may include a substantially linear, elongated thermal segment disposed on or embedded in a portion of the elongate body. As shown in FIG. 1b, the anchoring element may include a malleable or non-compliant disc. FIG. 1c illustrates the anchoring element defining one or more extendable protrusions or fingers for engaging a targeted tissue region. Each of these variations may include an internal chamber or passage for the introduction of a fluid or coolant to facilitate cryoadhesion between the anchoring element 26a and a tissue structure.

In addition, the elongate body 16 may include a guide wire or stylet lumen 32 movably disposed within and/or extending along at least a portion of the length of the elongate body 16 for over-the-wire applications and/or for use with a stylet. The guide wire lumen 32 may define a proximal end and a distal end, and the guide wire lumen 32 may be movably disposed within the elongate body 16 to also facilitate or allow manipulation of the anchoring element 26a. For example, the anchoring element 26a may include a proximal end coupled to a first portion 34 of the elongate body 16 while the distal portion 20 of the anchoring element may be coupled to a second portion 36 of the elongate body 16 that is movable in conjunction with the movement of the guide wire lumen 32. That is, the first portion 34 of the elongate body 16 may be movable with respect to the second portion 36 of the elongate body 16, where the movement is actuated by or otherwise coupled to movement of the guide wire lumen 32. As such, due to the movable nature of the guide wire lumen 32 and/or the second portion of the elongate body 16 with respect to the first portion of the elongate body 16, any axial and/or longitudinal movement of the guide wire lumen 32 may act to extend or tension (and oppositely, retract or loosen) the anchor element 26a. As such, where the anchoring element 26a includes an expandable element, the guide wire lumen 32 and/or the second portion 36 of the elongate body 16 may be used to controllably extend or retract the expandable element from a lengthened state to a shortened state for ease of insertion, positioning, and/or removal of the medical device 12. Positioning and manipulation of the portions of the medical device at the distal portion 20 may also be performed by direct action onto the proximal end of the medical device and/or elongate body 16, through direct use of a handle for example.

The first and second portions of the elongate body 16, the anchoring element 26a, and/or the treatment/diagnostic element(s) 22 may also be controllably moved with respect to each other through other linked couplings, or may be completely separate and independent of one another. For example, the second portion 36 of the elongate body 16 may be at least partially slidably disposed within the first portion 34 of the elongate body 16 in a telescoping arrangement to allow the length of second portion (and thus the distal portion 20 and diagnostic/treatment element of the medical device 12) to be controllably selected and deployed to reach targeted tissue sties or structures once the anchoring element 26a is engaged. Further, the distal portion and the diagnostic/treatment element 22 may be separate from the elongate body 16. The diagnostic/treatment element 22 may be mounted or otherwise located on a secondary device or elongate body that is passable through the elongate body 16, allowing increased independent and separate operation between the anchoring element 26a and the distal treatment/diagnostic portion or element of the system 10. The controlled deployment and/or retraction of the second portion may be achieved through the use of one or more steering wires or other actuation mechanisms as known in the art.

Figure 2:
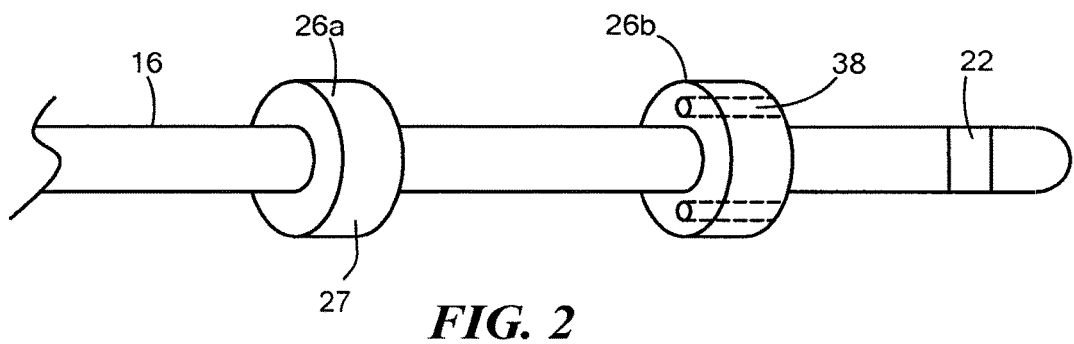
FIG. 2 is an illustration of an embodiment of a medical device constructed in accordance with the principles of the present invention.

Now referring to FIG. 2, the medical device 12 may include a second anchoring element 26b, such as an expandable element or other deployable/retractable structure, disposed on the elongate body 16 between the anchoring element 26a and the treatment/diagnostic element 22 at the distal portion 20. The second anchoring 26b element may be operated independently of the anchoring element 26a. To that end, the second anchoring element 26b may be in fluid communication with an independent arrangement of inflation lumen(s), exhaust lumen(s), and/or fluid sources (not shown), as well as independently operated steering or deflection mechanisms (not shown). The second anchoring element 26b may provide for additional engagement of a portion of the medical device 12 to a desired tissue region or anatomical structure while still allowing the treatment/diagnostic element 22 to be maneuvered for use. The second anchoring element 26b, or portions of the medical device 12 in proximity to the second anchoring element, may define one or more perfusion passages 38 providing for the flow of blood or other fluids through and/or around the medical device 12 when in use in constricted areas, such as an ostium or other portion of the coronary sinus.

Of note, while an example of a suitable anchoring element may include an expandable or inflatable member or balloon, other controllably deployable and/or retractable structures and mechanisms may be employed to facilitate engagement of a portion of the medical device 12 with a desired tissue region or structure. For example, one or more arms (not shown) may be extendable from a portion of the elongate body 16, or the elongate body 16 may define one or more deformable regions (not shown) that can be bowed outward to contact and engage adjacent tissue structures.

Referring again to FIG. 1, the medical device 12 may include a handle 40 coupled to the proximal portion 18 of the elongate body 16, where the handle 40 may include an element such as a lever or knob 42 for manipulating portions of the elongate body 16 and/or additional components of the medical device 12 14. The handle 40 can further include circuitry for identification and/or use in controlling of the medical device 12 or another component of the system 10. Additionally, the handle 40 may be provided with a fitting 44 for receiving a guide wire that may be passed into the guide wire lumen 32. The handle 40 may also include connectors 46 that are matable directly to a fluid supply/exhaust and/or control unit 14 or indirectly by way of one or more umbilicals.

Continuing to refer to FIG. 1, the medical device 12 may include an actuator element 48 that is movably coupled to the proximal portion 18 of the elongate body 16 and/or the handle 40. The actuator element 48 may be further coupled to the guide wire lumen 32 and/or second portion of the elongate body 16 such that manipulating the actuator element in a longitudinal direction causes the guide wire lumen 32 and/or the second portion of the elongate body 16 to slide towards either of the proximal or distal portions of the medical device 12. As a portion of either and/or both the anchoring elements 26a, 26b may be coupled to the guide wire lumen 32 and/or the second portion of the elongate body 16, manipulation of the actuator element 48 may further provide for the controllable deployment and retraction of the anchoring element(s). The actuator element 48 may include a thumb-slide, a push-button, a rotating lever, or other mechanical structure for providing a movable coupling to the elongate body 16 (or portion thereof), the handle 40, the guide wire lumen 32, and/or the anchoring element(s) 26a, 26b. Moreover, the actuator element 48 may be movably coupled to the handle 40 such that the actuator element is movable into individual, distinct positions, and is able to be releasably secured in any one of the distinct positions.

The system 10 may further include one or more sensors to monitor the operating parameters throughout the system 10, including for example, pressure, temperature, flow rates, volume, or the like in the control unit 14 and/or the medical device 12, in addition to monitoring, recording or otherwise conveying measurements or conditions within the medical device 12 or the ambient environment at the distal portion 20 or anchoring elements of the medical device 12. For example, a temperature sensor 50 may be disposed in thermal communication with a portion of the anchoring element. The sensor(s) may be in communication with the control unit 14 for initiating or triggering one or more alerts or therapeutic delivery modifications during operation of the medical device 12. One or more valves, controllers, or the like may be in communication with the sensor(s) to provide for the controlled dispersion or circulation of fluid through the injection lumens/fluid paths of the medical device 12. Such valves, controllers, or the like may be located in a portion of the medical device 12 and/or in the control unit 14.

In an exemplary system, a fluid supply including a coolant, cryogenic refrigerant, or the like, an exhaust or scavenging system (not shown) for recovering or venting expended fluid for re-use or disposal, as well as various control mechanisms for the medical device 12 and the anchoring element(s) may be housed in the control unit 14. In addition to providing an exhaust function for the fluid supply, the control unit 14 may also include pumps, valves, controllers or the like to recover and/or re-circulate fluid delivered to the handle 40, the elongate body 16, anchoring element(s) and/or treatment/diagnostic element(s) 22 of the medical device 12. The control unit 14 may also include the power source 24 in electrical communication with the electrode(s). The control unit 14 may include one or more controllers, processors, and/or software modules containing instructions or algorithms to provide for the automated operation and performance of the features, sequences, or procedures described herein.

Figure 3:
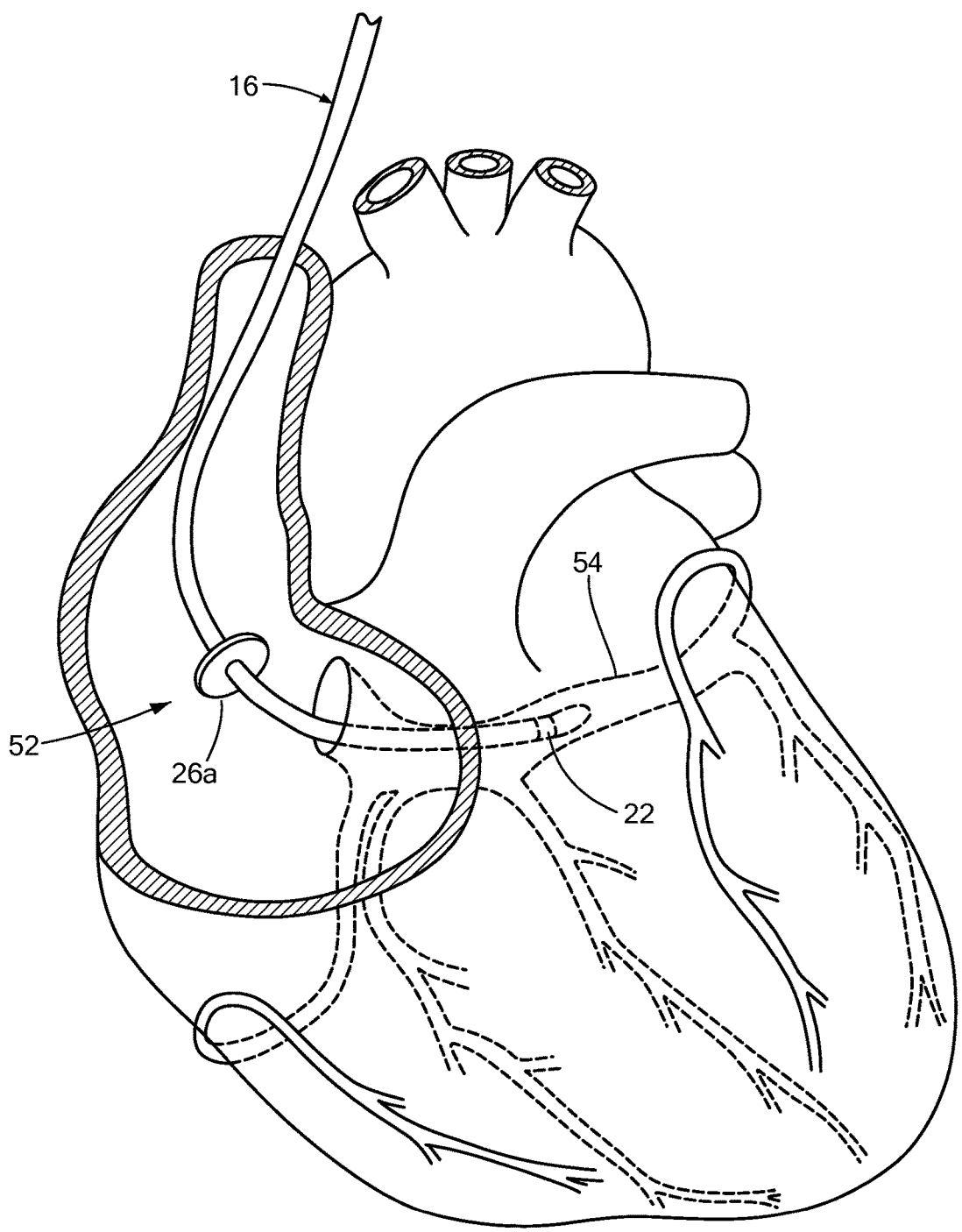
FIG. 3 is an exemplary use of an embodiment of a medical system in accordance with the principles of the present invention.
Figure 4:
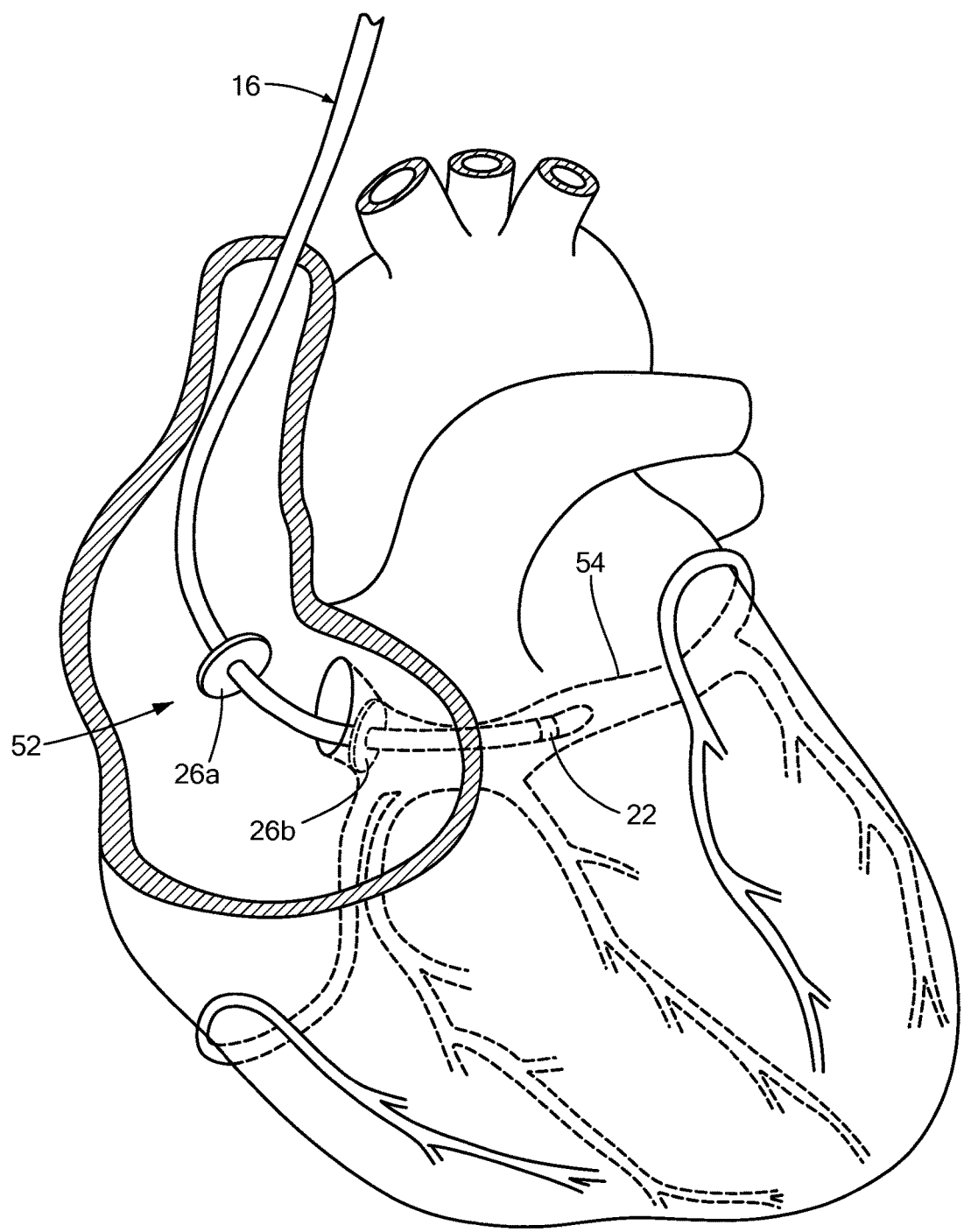
FIG. 4 is another exemplary use of an embodiment of a medical system in accordance with the principles of the present invention.

Now referring to FIGS. 3-4, exemplary methods of use of the medical system 10 are illustrated. The medical device may be positioned near a region of tissue targeted for a therapeutic or diagnostic procedure, and the anchoring element(s) 26a, 26b may be cryoadhered to a portion of the tissue before, during, or after placement or positioning of the treatment/diagnostic element 22. For example, as shown in FIG. 3, a portion of the elongate body 16 may be routed through the vasculature of a patient and into a chamber of the heart, such as the right atrium 52. The introduction, routing, and/or positioning of the medical device 12 may be facilitated with one or more sheaths, introducer devices, and/or other secondary devices. The medical device 12 may be positioned such that the anchoring element is in proximity to a region of the atrial wall near the coronary sinus 54, while the distal portion 20 of the medical device 12 including the treatment/diagnostic element 22 is directed into the coronary sinus 54. The handle 40 and/or proximal end 18 of the medical device 12 may be used to exert a pressure or torque on the anchoring element 26a and/or the treatment/diagnostic element 22 to obtain a desired location or position of the device 12 with respect to the surrounding anatomy. Once in a generally desired position, the anchoring element 26a may be actuated or otherwise operated to engage the atrial wall or surrounding tissue. For example, where the anchoring element includes the expandable element, a cryogenic cooling fluid may be introduced into the expandable element to significantly reduce the temperature of the anchoring element. The reduced temperature promotes or otherwise results in cryoadhesion between the cooled anchoring element and the tissue. Of note, the reduced temperatures obtained in the anchoring element 26 may be sufficiently cold to promote adhesion between the tissue and the anchoring element 26, while minimizing the likelihood of creating a permanent tissue lesion or otherwise adversely affecting cardiac conduction or function through the adhered tissue segment. Such temperatures may include, for example, those temperatures typically used for cardiac mapping using a cryogenic device, e.g., approximately −25° C. or higher.

Now referring to FIG. 4, where multiple anchoring elements are included, an exemplary method of use may include positioning the anchoring elements into a generally desired position. For example, the anchoring element 26a may be positioned adjacent the atrial wall, while the second anchoring element 26b may be routed into the ostium of the coronary sinus, with the distal portion 20 of the elongate body 16 extending even further into the coronary sinus. The anchors may then be deployed, which may include the introduction of a coolant into the individual anchors to effectuate a cryoadhesive engagement between the individual anchoring elements and their surrounding tissue. To reduce any undesired effects from the obstruction of blood flow through the coronary ostium, external fluid flow may be perfused through the perfusion passages 38 of the second anchoring element 26b and/or portion of the elongate body 16.

Engaging the tissue with the anchoring element(s) provides a substantially fixed position to aid in either securing the previously-attained position of the distal portion 20 of the medical device 12 or providing a substantially secure location from which the distal portion 20 of the elongate body 16 and thus the diagnostic/treatment element can be moved around to more effectively reach a targeted tissue location, such as a branch of the coronary sinus and/or blood vessels connected or otherwise in proximity thereto. Alternatively, the anchoring element(s) can be used to secure the device after a desirable position of the proximal and/or distal portion has been attained. Moreover, while a particular example of a targeted tissue location and/or structure can include cardiac tissue and the coronary sinus, the anchoring and positioning of the medical device may be implemented in other areas, including a trans-septal crossing site (such as an intraventricular septum), an intravascular insertion point, and an epicardial-to-endocardial site (and vice versa), for example.

Once the medical device 12 has been suitably anchored and the distal portion 20 directed to the targeted site, the treatment/diagnostic element 22 may then be used in accordance with the aim of the particular procedure. Such procedures may include, for example, electrically stimulating or pacing cardiac tissue, electrically mapping aberrant electrical activity, ablating a problematic tissue segment, measuring an electrical characteristic of the tissue, or the like, using the components of the medical system 10 as described herein.

Upon completing the selected treatment or diagnostic regimen, the anchoring elements may be retracted or otherwise released from their engagement with the tissue. Where cryoadhesion is the engagement mechanism, removal of the anchoring element(s) 26a, 26b may be prolonged until a temperature of the anchoring element(s) or tissue has reached a predetermined, thawed temperature to reduce the likelihood of any unwanted injury to the tissue that could otherwise result. Retraction and/or removal of the anchoring elements, the treatment/diagnostic element 22, and/or portions of the elongate body 16 may be facilitated, at least in part, through the manipulation of the handle, actuator element 48, the relative movement between portions of the elongate body 16, and/or other steering modalities as described herein.

Of note, maneuvering and directing the medical device 12 to the desired locations may be aided in part by fluoroscopy or other imaging means to the extent portions of the device 12 and/or surrounding tissue structures can be visualized. For example, the formation of ice crystals between the medical device 12 and the adhered tissue can be imaged or otherwise located using imaging methodologies able to distinguish the properties of frozen ice or tissue segments as compared to non-frozen tissue regions, such as ultrasound.

In addition, the anchoring element(s) 26 and/or the treatment/diagnostic element 22 may provide reference points for locating and/or mapping a position of the medical device 12. For example, the medical device may be used in conjunction with a position sensing module or system 55 that is operable to map and illustrate mapped and saved points. The position sensing system can be used to determine the location or position of the anchoring element(s) 26 and/or the treatment/diagnostic element 22 by generating a voltage in a patient and calculating an impedance at the anchoring element(s) 26 and/or the treatment/diagnostic element 22. The calculated impedance may then be used to determine the position of the electrode as in a patient or other appropriate conducting medium.

Figure 5:
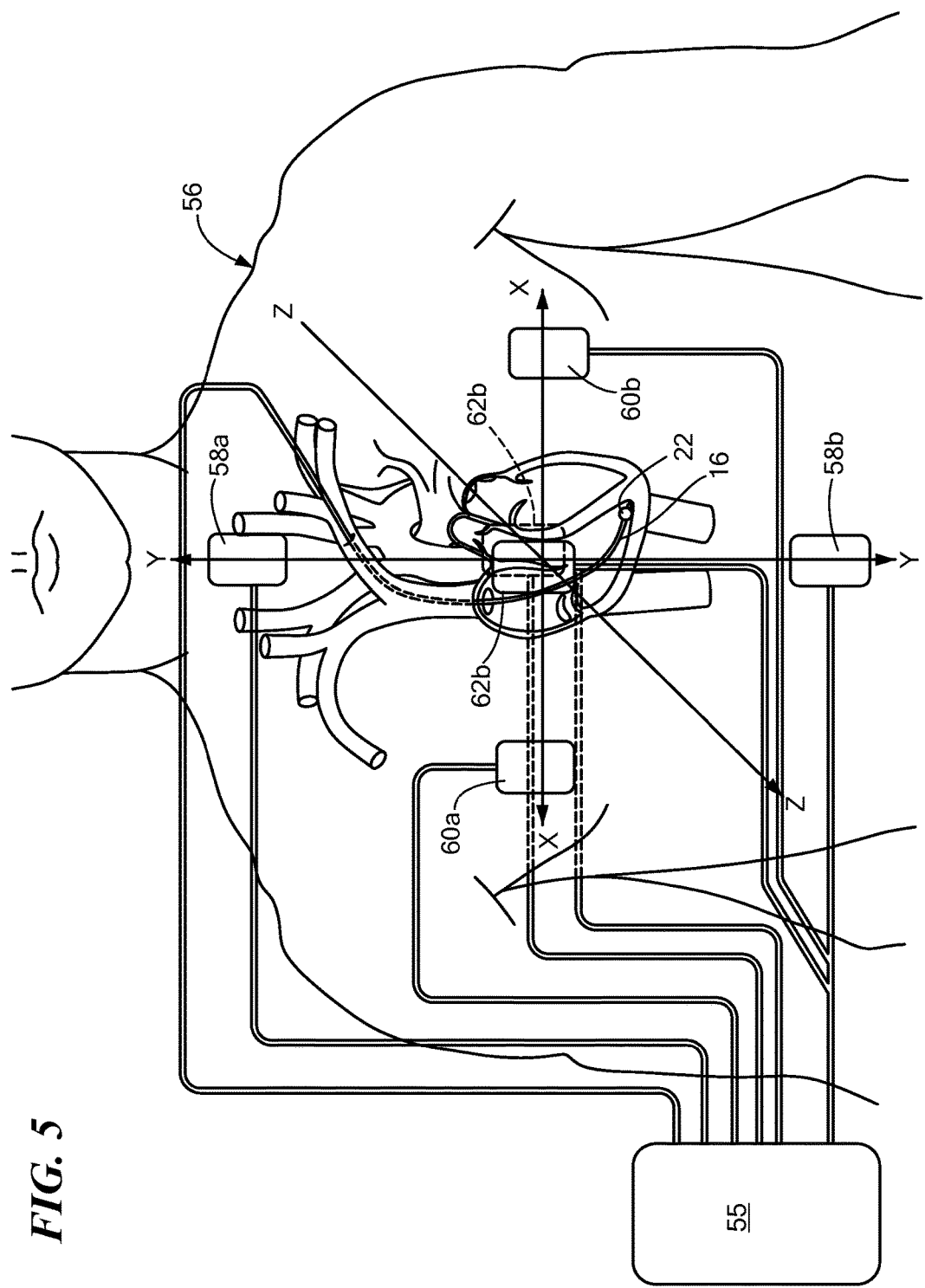
FIG. 5 is an illustration of an embodiment of a position sensing system constructed in accordance with the principles of the present invention.

In particular, as shown in FIG. 5, a portion of the anatomy of a patient 56 can be mapped by identifying a plurality of points to generate a map within the patient 56 by determining a relative location of the medical device 12. The plurality of points can be illustrated individually, or sequentially, or a surface can be illustrated with or without the plurality of points to illustrate or identify a portion of the anatomy of the patient 56. The map data can be generated or acquired with the position sensing system 55 that can acquire multiple points of or within the patient 56. The position sensing system 55 can obtain or otherwise measure voltage, impedance, acoustic properties (e.g., sound and ultrasound), time-of-travel information, magnetic field strengths, for example. The position sensing system 55 can include an impedance or electrical potential (EP) system, an electromagnetic (EM), and/or optical tracking system that can be integrated with or operate independently and separate from the control unit 14.

The position sensing system 55 may include a processor, controller or driving unit that includes one or more input or output connectors to interconnect with a plurality of current conducting or drive patches or electrodes connected directly with the patient 56, and may also be coupled to the anchoring element(s) 26 and/or the treatment/diagnostic element 22 to obtain, sense, or otherwise record an electrical measurement or property thereof during a procedure. The current patches/reference electrodes can include electrically conductive segments placed on or in the patient to create three substantially orthogonal voltage or current axes within the patient 56. For example, a first y-axis patch 58a and a second y-axis patch 58b can be positioned on an exterior of the patient 56 to form a y-axis (such as an axis that is generally superior-inferior of a patient as illustrated in FIG. 5) with a conductive path such that the conducted current establishes a voltage potential gradient substantially along this axis and between the patches 58a and 58b. A related y-axis current flows from the first y-axis patch 58a to the second y-axis patch 58b substantially along the y-axis. Likewise, a first x-axis patch 60a and a second x-axis patch 60b can be connected with the patient 56 to create a x-axis (such as an axis that is generally medial-lateral of a patient) with a voltage gradient substantially along the x-axis between the patches 60a and 60b and a corresponding x-axis current flowing between patches 60a and 60b. Finally, a first z-axis patch 62a and a second z-axis patch 62b can be connected with a patient 56 to create a z-axis (such as an axis that is generally anterior-posterior of a patient) with a voltage potential gradient substantially along the z-axis between the patches 62a and 62b with a corresponding z-axis current flowing between the patches 62a and 62b. The three axes are generally formed to have an organ or area of interest that the common intersection or origin of each of the axes x, y, z. Accordingly, the patches can be positioned on or in the patient 56 to achieve the selected placement of the axes x, y, z relative to the patient 56. Alternatively to surface-positioned reference electrodes or patches, an electrically conductive segment or electrode may be placed inside the patient in the form of a secondary catheter or medical device, a permanently implanted electrically conductive segment or lead, or the like.

The current applied between the related patches generates a small or micro-current, which can be about 1 microampere (muA) to about 100 milliamperes (mA), in the patient along the axis between the respective patch pairs. The induced current can be of a different frequency for each of the related patch pairs to allow for distinguishing which axis is being measured or can be of a single frequency and time multiplexed. The current induced in the patient 56 will generate a voltage gradient across different portions, such as the heart, that can be measured with an electrically conductive portion of the anchoring element(s) 26 and/or the treatment/diagnostic element 22. The sensed voltage can be used to identify a position of the anchoring element(s) 26 and/or the treatment/diagnostic element 22 along an axis (whereby each axis can be identified by the particular frequency of the current being measured) to generally determine a position along each of the three axes. Although a voltage can be sensed, an impedance can also be calculated or measured to determine a location in a similar manner. The position of the anchoring element(s) 26 and/or the treatment/diagnostic element 22 with respect to each of the three axes can be used as map data for the surrounding physiological area. The anchoring element(s) 26 and/or the treatment/diagnostic element 22 can be moved through various portions in the patient 56 while obtaining, sensing or otherwise recording the voltages, substantially continuously or as selected intervals, among the three axes to determine multiple three dimensional positions of the anchoring element(s) 26 and/or the treatment/diagnostic element 22.

The saved points may be used to create a map generated with the anchoring element(s) 26a, 26b and/or the treatment/diagnostic element 22 that can be used to determine a location of a later positioned anchoring element(s) 26 and/or the treatment/diagnostic element 22 (such as in a subsequent follow-up procedure). The discussion herein may refer to map data or map data points and will be understood to include individual acquired data points, illustrated individual or managed points an algorithm process applied to acquired data points to improve visual display by eliminating regions of especially high density and useful in modulating characteristics of rendered surfaces, a rendered surface, or any appropriate manner of illustrating the acquired map data. Once the map has been created of the patient 56 or a portion of the patient 56, either with or without a surface rendered relative to the individual points, a procedure can be guided or navigated using the map data.

The map data can be used to identify various anatomical features. In addition, instruments, including the medical device 10 and/or other instruments separate or complementary to the medical device 12 in a common procedure or subsequent procedures, can be navigated relative to the patient 56 using the map data. For example, a sterilized or "new" medical device 12 may be used in a later procedure to create a second map having one or more points using the methodology described above. The second map may be compared and registered to the first map to match the location and reference points from the first procedure to the locations and reference points in the second procedure. Significant physiological changes are unlikely to occur to anatomical structures or features (such as the superior vena cava, inferior vena cava, the coronary sinus, and/or portions thereof) between procedures, which allows such anatomical structures to be matched or synchronized between the two maps. The second procedure can thus proceed with knowledge of the previous locations and reference points where therapy and/or diagnostic measurements were conducted in the earlier procedure with respect to the medical device as positioned in the second procedure. In a particular example, obtaining a second map, registering it or matching it the first map, and proceeding with the secondary procedure can allow a physician or user to "touch up" or otherwise create additional ablative segments in the treatment of an arrhythmia to lesions or specific treatment areas or location initially created during a first, previous procedure.

Identification of implants, ablation or cannulation procedures, or other procedures can be performed to guide initial procedures as well as providing a guiding, navigational history for later treatments or procedures. Accordingly, a procedure can be navigated and performed precisely and repeatably with the generated map data in an initial treatment as well as subsequent procedures. A display device (either separate or integral with the control unit 14, for example) can be used to display the map data and/or illustrate icons representing various portions or reference points relative to the patient 56. The registering or correlation between the two maps can be performed by one or more processors in the system 55, and presented to an end-user in a visual format. Moreover, the system 55 may include one or more storage components to store map data recorded or otherwise obtained during one or more procedures for later use in subsequent procedures. In addition, the map data can be generated in a substantially three dimensional or even four dimensional manner. Accordingly, the display can include a three dimensional viewing, simulated three dimensional viewing, or even four dimensional viewing, such as to illustrate a change in the patient 56 over time.

The map generated with the position sensing system can be used to guide or navigate the medical device 12 to a selected location without the use of other prior or concurrent imaging devices, such as an external fluoroscope, magnetic resonance imaging, ultrasound, as described in more detail in application Ser. No. 12/424,013, filed Apr. 15, 2009, entitled "LOCATING A MEMBER IN A STRUCTURE," the entirety of which is hereby incorporated by reference.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A method of operating a medical device in a patient, comprising:
   positioning an inflatable first chamber of a medical device adjacent a first tissue region, the first tissue region including cardiac tissue, the inflatable first chamber including an expandable portion that is electrically conductive, the expandable portion being configured to be expanded to a maximum cross-sectional diameter of the inflatable chamber when the medical device is in use;
   directing a cryogenic coolant through a first fluid flow path into the inflatable first chamber to expand the expandable portion of the inflatable first chamber;
   positioning an inflatable second chamber of the medical device adjacent a second tissue region, the second tissue region including a portion of the coronary sinus, the inflatable second chamber including an expandable portion that is configured to be expanded to a maximum cross-sectional diameter of the inflatable second chamber when the medical device is in use;
   directing a cryogenic coolant through a second fluid flow path into the inflatable second chamber to expand the expandable portion of the inflatable second chamber;
   anchoring the expanded inflatable first chamber to the first tissue region through cryoadhesion and anchoring the expanded inflatable second chamber to the second tissue region through cryoadhesion;
   positioning at least one of a diagnostic element and a therapeutic element of the medical device adjacent a third tissue region;
   operating the at least one of a diagnostic element and therapeutic element proximate to the third tissue region; and
   obtaining positional information from the expandable electrically conductive portion of the inflatable first chamber and transmitting the positional information from the electrically conductive portion of the inflatable first chamber to a position sensing system.

2. The method of claim 1, wherein the at least one of a diagnostic element and therapeutic element includes a thermal ablation element, and wherein operating the ablation element includes ablating at least a portion of the third tissue region.

3. The method of claim 1, wherein positioning the at least one of a diagnostic element and therapeutic element includes moving the at least one of a diagnostic element and therapeutic element with respect to the inflatable first chamber.

4. The method of claim 1, wherein the at least one of a diagnostic element and therapeutic element includes a cardiac lead.

5. The method of claim 1, further comprising measuring a temperature of the inflatable first chamber.

6. The method of claim 1, further comprising:
   obtaining positional information from the at least one of a diagnostic element and a therapeutic element; and
   storing the positional information.

7. The method of claim 6, wherein obtaining positional information from the at least one of a diagnostic element and a therapeutic element includes at least one of:
   conducting a current through the at least one of a diagnostic element and a therapeutic element; and
   measuring a voltage with the at least one of a diagnostic element and a therapeutic element.

8. The method of claim 7, wherein obtaining positional information from the at least one of a diagnostic element and a therapeutic element includes determining an impedance between i) the at least one of a diagnostic element and a therapeutic element and ii) a reference electrode positioned about the patient.

9. The method of claim 7, further comprising:
   registering the obtained positional information to a historical positional information set.

10. The method of claim 1, wherein obtaining positional information from the inflatable first chamber includes at least one of:
    conducting a current through at least a portion of the inflatable first chamber; and
    measuring a voltage with at least a portion of the inflatable first chamber.

11. The method of claim 10, wherein obtaining positional information from the inflatable first chamber includes determining an impedance between the expandable portion of the inflatable first chamber and a reference electrode located proximate to the patient.

12. A method of treating a patient, comprising:
    performing a first procedure, the first procedure including:
       positioning a first chamber of a first medical device adjacent a first tissue region, the first chamber including an expandable portion that is electrically conductive;
       expanding the expandable portion of the first chamber to a maximum diameter of the first chamber such that the expandable portion of the first chamber is in contact with the first tissue region;
       positioning a second chamber of the first medical device adjacent a second tissue region, the second chamber including an expandable portion and one or more perfusion apertures;
       expanding the expandable portion of the second chamber to a maximum cross-sectional diameter of the second chamber such that the expandable portion of the second chamber is in contact with the second tissue region;
       anchoring the first chamber to the first tissue region through cryoadhesion and anchoring the second chamber to the second tissue region through cryoadhesion;
       positioning at least one of a diagnostic element and a therapeutic element of the first medical device adjacent a third tissue region different from the first and second tissue regions;
       operating the at least one of a diagnostic element and therapeutic element proximate to the third tissue region;
       obtaining positional information from the expandable electrically conductive portion of the first chamber and the at least one of a diagnostic element and a therapeutic element;

generating a first map based on the positional information; and performing a second procedure, the second procedure including:

positioning the first chamber of the first medical device adjacent a fourth tissue region, the second tissue region and the fourth tissue region being substantially co-located;

expanding the expandable portion of the first chamber to the maximum cross-sectional diameter of the first chamber such that the expandable portion of the first chamber is in contact with the fourth tissue region;

positioning the second chamber of the first medical device adjacent a fifth tissue region;

expanding the expandable portion of the second chamber to the maximum cross-sectional diameter of the second chamber such that the expandable portion of the second chamber is in contact with the fifth tissue region;

anchoring the first chamber to the fourth tissue region through cryoadhesion and anchoring the second chamber to the fifth tissue region through cryoadhesion;

positioning the at least one of a diagnostic element and a therapeutic element adjacent a sixth tissue region different from the fourth and fifth regions;

operating the at least one of a diagnostic element and therapeutic element proximate to the sixth tissue region;

obtaining positional information from the electrically conductive portion of the first chamber at the at least one of a diagnostic element and a therapeutic element;

generating a second map based on the positional information; and registering the second map to the first map.

13. A method of treating cardiac tissue, comprising:

directing a distal portion of a medical device into a coronary sinus, the medical device including a first chamber and a second chamber;

positioning the first chamber of the medical device adjacent an atrial wall, the first chamber including an expandable portion that is electrically conductive and configured to be expanded to a maximum cross-sectional diameter of the first chamber when the device is in use;

directing a cryogenic coolant into the first chamber;

anchoring the first chamber to the atrial wall through cryoadhesion;

positioning the second chamber of the medical device adjacent a tissue region in the coronary sinus, the second chamber including an expandable portion that is configured to be expanded to a maximum cross-sectional diameter of the second chamber when the medical device is in use;

directing a cryogenic coolant into the second chamber;

anchoring the second chamber to the tissue region in the coronary sinus through cryoadhesion;

positioning an implantable cardiac lead through at least a portion of the coronary sinus with the distal portion of the medical device; and transmitting positional data from the electrically conductive portion of the first chamber to a position sensing system.

* * * * *

UNITED STATES PATENT AND TRADEMARK OFFICE
CERTIFICATE OF CORRECTION

| | | |
|---|---|---|
| PATENT NO. | : 9,655,666 B2 | Page 1 of 1 |
| APPLICATION NO. | : 12/915327 | |
| DATED | : May 23, 2017 | |
| INVENTOR(S) | : H. Toby Markowitz | |

It is certified that error appears in the above-identified patent and that said Letters Patent is hereby corrected as shown below:

On the Title Page

The ASSIGNEE name is listed incorrectly as "Medtronic Ablatio Frontiers LLC". Please replace the name with the following:
--Medtronic Ablation Frontiers LLC--

Signed and Sealed this
Third Day of October, 2017

Joseph Matal
*Performing the Functions and Duties of the
Under Secretary of Commerce for Intellectual Property and
Director of the United States Patent and Trademark Office*